US009452235B2

United States Patent
Veen et al.

(10) Patent No.: US 9,452,235 B2
(45) Date of Patent: Sep. 27, 2016

(54) INCUBATOR WITH AIR PURIFICATION

(75) Inventors: Jeroen Veen, Nijmegen (NL); Alberto Fazzi, Eindhoven (NL); Ganesan Ramachandran, Bangalore (IN)

(73) Assignee: Koninklijke Philips N.V., Eindhoven (NL)

( * ) Notice: Subject to any disclaimer, the term of this patent is extended or adjusted under 35 U.S.C. 154(b) by 248 days.

(21) Appl. No.: 14/343,434

(22) PCT Filed: Sep. 6, 2012

(86) PCT No.: PCT/IB2012/054605
§ 371 (c)(1),
(2), (4) Date: Mar. 7, 2014

(87) PCT Pub. No.: WO2013/038305
PCT Pub. Date: Mar. 21, 2013

(65) Prior Publication Data
US 2014/0212329 A1 Jul. 31, 2014

Related U.S. Application Data

(60) Provisional application No. 61/535,552, filed on Sep. 16, 2011.

(51) Int. Cl.
*A61L 9/20* (2006.01)
*A61G 11/00* (2006.01)

(52) U.S. Cl.
CPC ............... *A61L 9/20* (2013.01); *A61G 11/00* (2013.01); *A61G 2200/14* (2013.01); *A61G 2203/44* (2013.01); *A61G 2203/46* (2013.01); *A61G 2210/90* (2013.01); *A61L 2209/11* (2013.01); *A61L 2209/12* (2013.01); *A61L 2209/14* (2013.01); *A61L 2209/20* (2013.01)

(58) Field of Classification Search
CPC ................................. A61L 9/20; A61G 11/00
USPC ............................................. 250/435; 600/22
See application file for complete search history.

(56) References Cited

U.S. PATENT DOCUMENTS

| 2,243,999 A | 6/1941 | Chapple |
| 3,710,791 A | 1/1973 | Deaton |
| 6,508,989 B1 | 1/2003 | Urrusti et al. |

FOREIGN PATENT DOCUMENTS

| FR | 1094444 A | | 5/1955 |
| GB | 1501281 A | | 2/1978 |
| JP | 10113096 A | * | 5/1998 |
| RU | 79420 U1 | | 1/2009 |
| RU | 2376969 C1 | | 12/2009 |
| WO | 2011031167 A1 | | 3/2011 |

OTHER PUBLICATIONS

English language machine translation of JP 10113096 A, published May 1998.*

(Continued)

*Primary Examiner* — Sean E Conley (57) ABSTRACT

Systems and methods for air purification within an incubator using germicidal irradiation from an ultra-violet (UV) light source that is integrated in a path from ambient air into the cavity of an incubator.

6 Claims, 6 Drawing Sheets

(56) References Cited

OTHER PUBLICATIONS

Farhad Memarzadeh et al; "Applications of Ultraviolet Germicidal Irradiation Disinfection in Health Care Facilities: Effective Adjunct, But Not Stand-Alone Technology", American Journal of Infection Control, Jun. 2010, pp. S13-S24.

"What Microorganisms are Deacativated by Germicidal Ultraviolet Light", ultraviolet.com.
"HEPA", Wikipedia Encyclopedia.
Lynne Sehulster et al; "Guidelines for Environmental Infection Control in Health-Care Facilities", Recommendations of CDC and the Healthcare Infection Control Practices Advisory Committee, Jun. 6, 2003, pp. 1-60.

\* cited by examiner

INCUBATOR WITH AIR PURIFICATION

The present disclosure pertains to systems and methods for purifying air within an incubator, and, in particular, to providing germicidal irradiation of potentially contaminated ambient air on its way into the cavity of an incubator by ultra-violet radiation.

It is well known that incubators are indispensable to keep infants, including neonates, safe, warm, comfortable, and/or healthy, especially in NICU environments. It is well known that an infant is vulnerable to infections. It is well known that bacterial organisms, viral organisms, and other pathogenic organisms can cause infections and, at least in some cases, can be transmitted through airborne transmission of ambient air containing contaminated particles. It is well known that environments that commonly employ incubators, such as, e.g., hospitals, commonly are plagued by a wide range of pathogenic organisms. It is well known that micro-filters can only filter particles down to a particular particle size, which implies limited effectiveness in light of the range of pathogenic organisms and the range of corresponding particle sizes.

Accordingly, it is an object of one or more embodiments of the present disclosure to provide an incubator system configured to purify air. The incubator system includes a plurality of walls and a base, the base supporting the walls, the base and walls forming a cavity, a first ultra-violet (UV) light source, one or more processors, and a light module. The base and/or one or more of the walls may form a first path from ambient air into the cavity. The UV light source may be arranged along the first path and configured such that, responsive to the first UV light source being activated, the first UV light source provides germicidal irradiation of air within the first path, and such that UV radiation emitted from the first UV light source substantially does not impinge on an infant within the cavity. The light module may be configured to control operation of the first UV light source.

It is yet another aspect of one or more embodiments of the present disclosure to provide a method for purifying air within an incubator system. The method includes supporting an infant within a cavity formed by a plurality of walls and a base; guiding ambient air into the cavity using a first path provided by the base and/or one or more of the walls; emitting UV radiation using a first ultra-violet (UV) light source; and providing the emitted UV radiation to the first path to provide germicidal irradiation of air within the first path, such that UV radiation emitted from the first UV light source substantially does not impinge on an infant within the cavity.

It is yet another aspect of one or more embodiments to provide a system configured for purifying air within an incubator system. The system includes means for forming a cavity, means for guiding ambient air into the cavity, and means for providing germicidal irradiation of air within the means for guiding ambient air into the cavity, responsive to the means for providing germicidal irradiation being activated, such that UV radiation substantially emitted by the means for providing germicidal irradiation does not impinge on an infant within the cavity.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals may designate corresponding parts in the various figures. It is to be expressly understood, however, that the drawings are for the purpose of illustration and description only and are not intended as a definition of any limits.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
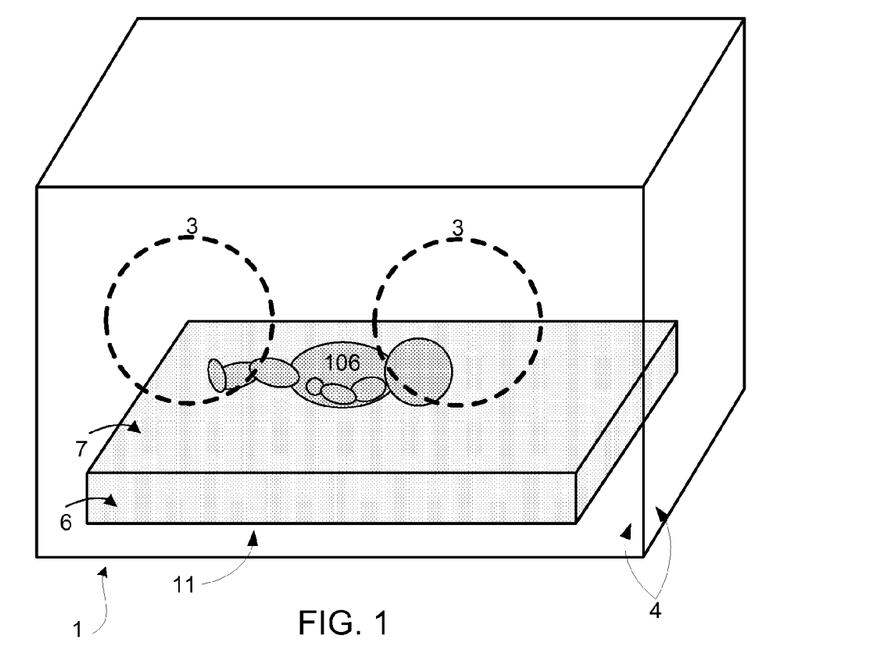
FIG. 1 illustrates an incubator.

FIG. 1 illustrates an incubator 1. Incubator 1 may be configured to protect and/or warm a subject, such as, e.g. infant 106. Incubator 1 may include a subject support structure 6, a plurality of transparent walls 4 and a base 2 forming a cavity 11, access windows 3, and/or other components. Subject support structure 6 may include, e.g., a mattress. Subject support structure 6 may be interchangeably referred to as mattress 6 throughout. Mattress 6 may include a top surface 7 that engages infant 106 during use of incubator system 10. Incubator system 10 may include one or more of a heater, a thermometer, a (UV) light source, a camera, and/or other components (not shown in FIG. 1).

Figure 2:
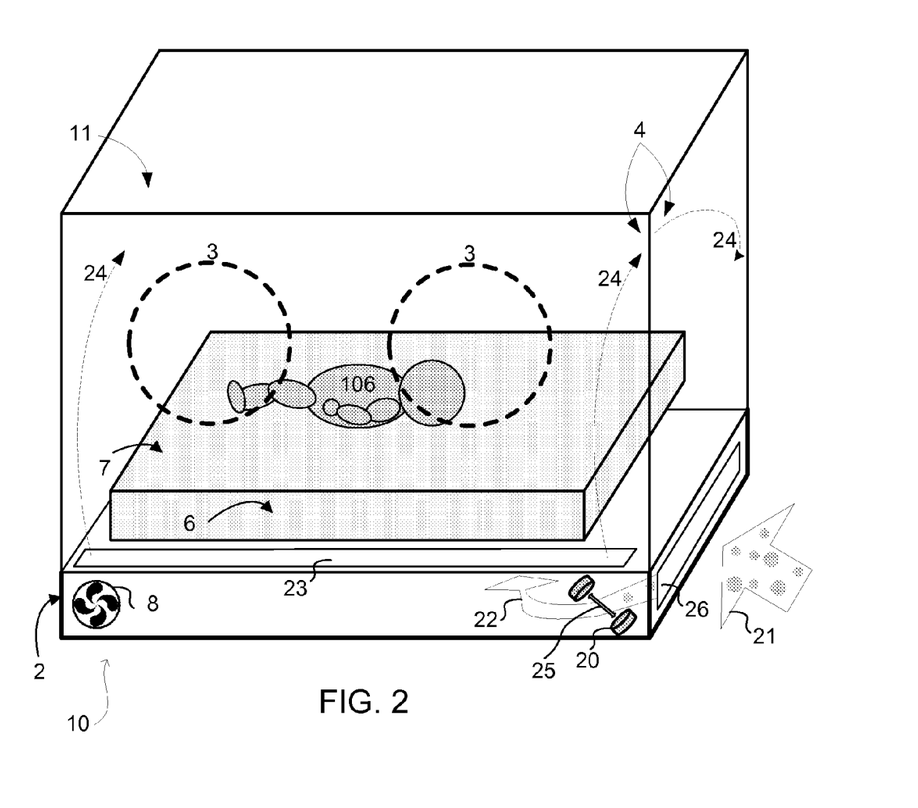
FIG. 2 illustrates an incubator system in accordance with one or more embodiments described herein.

FIG. 2 illustrates components of an incubator system 10 in accordance with one or more embodiments described herein, configured to provide air purification within cavity 11. Incubator system 10 may be configured to protect and/or warm a subject, such as, e.g. infant 106. Incubator system 10 may include a base 2 arranged to support the plurality of walls 4, a fan 8 to circulate air within cavity 11, an air inlet 26, a path 22 from ambient air 21 to cavity 11, one or more UV light sources 20, an air distribution panel 23, and/or other components. Base 2 and one or more walls 4 may form and/or include path 22 from ambient air 21 to cavity 11. Incubator system 10 may include one or more of a heater (not shown in FIG. 2), a camera (not shown in FIG. 2), one or more processors 110 (see FIG. 3), one or more sensors 142 (see FIG. 3), a user interface 120 (see FIG. 3), an electronic storage 130 (see FIG. 3), a light module 112 (see FIG. 3), and/or other components (not shown in FIG. 2).

Ambient air 21 in FIG. 2, which may potentially be contaminated by pathogenic organisms, may enter incubator system 10 via air inlet 26. Ambient air 21 may follow path 22 from air inlet 26 into cavity 11. Air may enter cavity 11 through air distribution panel 23. An air circulation device, such as, e.g., fan 8, may be used to circulate air within cavity 11. In FIG. 2, circulated air is depicted by dotted arrows labeled 24. One or more UV light sources 20 may be arranged along path 22 to provide germicidal irradiation of air within path 22, such that UV radiation 25 emitted from the one or more UV light sources 20 substantially does not impinge on infant 106 within cavity 11.

Note that electromagnetic radiation emitted by real-world light sources, as opposed to simplistic theoretical models of light sources, may have a non-deterministic distribution of its intensity and/or (beam) direction. Note furthermore that emitting a beam of electromagnetic radiation may be considered a stochastic event governed by a probability distribution. Nonetheless, this lack of substantial impingement may imply that about at least 99%, about at least 95%, about at least 90%, about at least 80%, and/or other percentages of electromagnetic radiation within a range of germicidal frequencies and/or electromagnetic radiation emitted by one or more light sources 20 does not impinge on infant 106 within cavity 11. Note that the positioning, orientation, direction, angle, and/or number of UV light sources 20 depicted in FIG. 2 are meant to be exemplary, not limiting.

Figure 3:
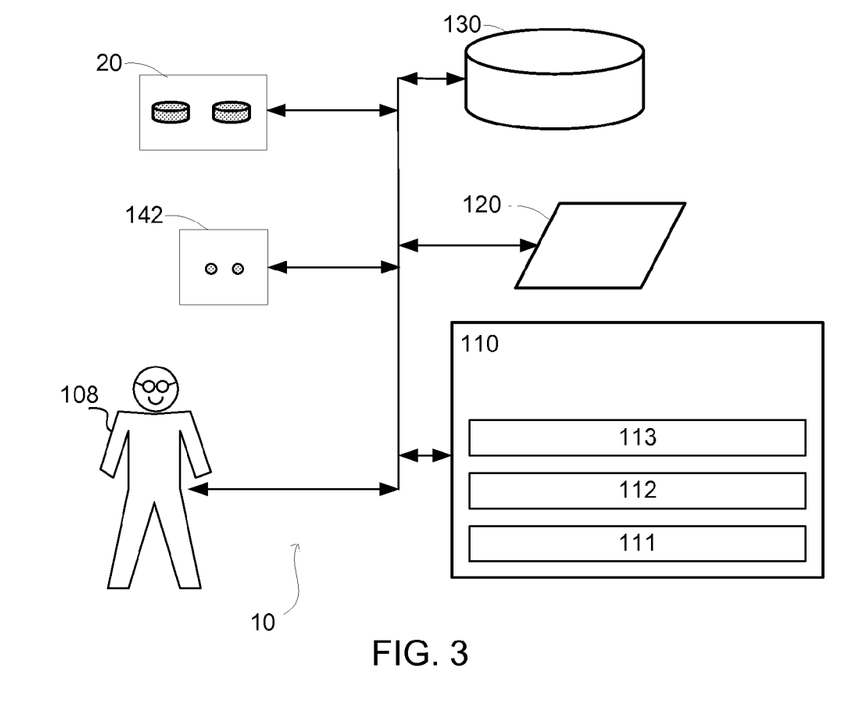
FIG. 3 schematically illustrates components of an incubator system in accordance with one or more embodiments described herein.

FIG. 3 schematically illustrates components of an incubator system 10 in accordance with one or more embodiments described herein. Incubator system 10 in FIG. 3 may include a plurality of walls 4 and a base 2 (not shown in FIG. 3) which may form a cavity 11 (not shown in FIG. 3), one or more sensors 142, one or more UV light sources 20, a user interface 120, an electronic storage 130, one or more processors 110, and/or other components.

Sensor(s) 142 of incubator system 10 in FIG. 3 may be configured to generate output signals conveying measurements related to the status of infant 106, the status of air within cavity 11, the status of incubator system 10, and/or medical parameters related to infant 106 and/or the environment within cavity 11. As a non-limiting example, sensors 142 may generate one or more output signals conveying information related to a position of infant 106 within cavity 11. In some embodiments, sensors 142 may generate one or more output signals conveying blockage information related to whether a blockable path from ambient air into cavity 11 is blocked. In some embodiments, sensors 142 may generate one or more output signals conveying purification information related to air quality within cavity 11. Sensors 142 may include one or more of a temperature sensor, a weight sensor, a still-image camera, a video camera, and/or other sensors.

The illustration of sensor 142 including two members in FIG. 3 is not intended to be limiting. Incubator system 10 may include a single sensor. In some embodiments sensor 142 includes a plurality of more than two sensors operating as described above by generating output signals conveying a variety of information. Resulting signals or information from sensors 142 may be transmitted to processor 110, user interface 120, electronic storage 130, and/or other components of incubator system 10. This transmission can be wired and/or wireless.

One or more UV light sources 20 of incubator system 10 in FIG. 3 may be configured such that ultra-violet electromagnetic radiation emitted by the one or more UV light sources provides germicidal irradiation of air within path 22, and such that emitted UV radiation substantially does not impinge on infant 106 within cavity 11. UV light sources 20 may be configured to have a controllable level of intensity, a controllable direction and/or angle of illumination, a controllable selection of illumination spectra, and/or other controllable illumination characteristics and/or illumination parameters.

Figure 4:
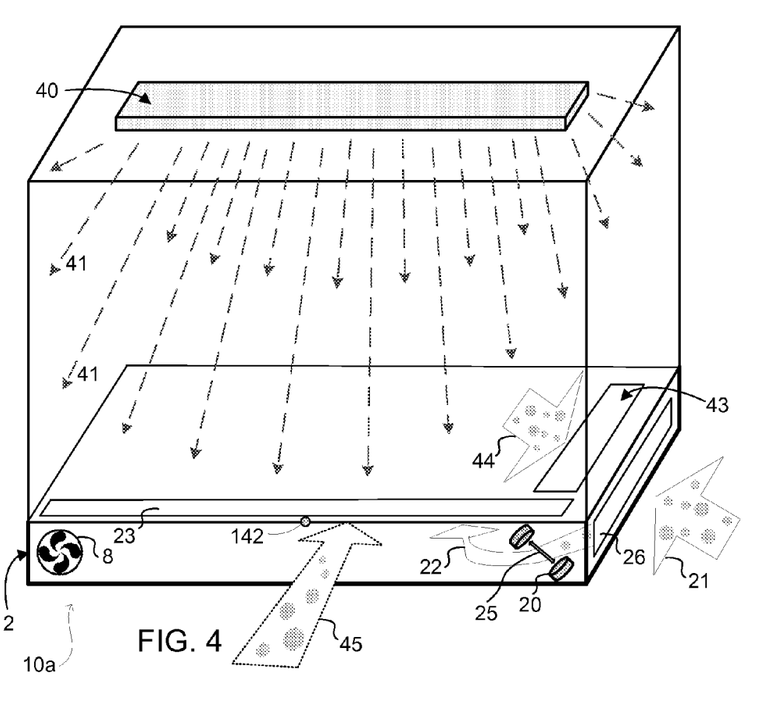
FIG. 4 illustrates an incubator system in accordance with one or more embodiments described herein.

In some embodiments, one or more UV light sources 20 in incubator system 10 may be arranged to provide germicidal irradiation for air circulated within cavity 11. By way of illustration, FIG. 4 illustrates an incubator system 10a that includes a redistribution panel 43 through which (possibly contaminated) air 44 within cavity 11 may be guided such that one or more UV light sources 20 may provide germicidal irradiation. In some embodiments, incubator system 10 includes a secondary UV light source arranged such that UV radiation emitted provides germicidal irradiation within cavity 11, obviously when infant 106 is not present within cavity 11. By way of illustration, FIG. 4 illustrates an incubator system 10a that includes a secondary UV light source 40 that emits UV radiation 41 (depicted in FIG. 4 by multiple dotted arrows) responsive, at least, to a determination that infant 106 is not present within cavity 11. Alternatively, and/or simultaneously, emission of UV radiation 41 may be responsive to determinations that the incubator system 10a is closed, a feature within the incubator walls is activated to absorb or reflect UV radiation, and/or the exterior of incubator system 10a is covered, and/or other determinations that indicate UV radiation 41 will not impinge on anyone or anything unintentionally.

User interface 120 of incubator system 10 in FIG. 3 may be configured to provide an interface between incubator system 10 and a user (e.g., user 108, a caregiver, a healthcare provider, a therapy decision-maker, etc.) through which the user can provide information to and receive information from incubator system 10. This enables data, results, and/or instructions and any other communicable items, collectively referred to as "information," to be communicated between the user and incubator system 10. An example of information that may be conveyed to user 108 is a report detailing the changes in monitored air quality throughout a period during which infant 106 is present within incubator system 10. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 by user interface 120 in the form of auditory signals, visual signals, tactile signals, and/or other sensory signals, or any combination thereof.

By way of non-limiting example, user interface 120 may include a radiation source capable of emitting light. The radiation source may include, for example, one or more of at least one LED, at least one light bulb, a display screen, and/or other sources. User interface 120 may control the radiation source to emit light in a manner that conveys to user 108 information related to the determined level of air quality.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into incubator system 10 from removable storage (e.g., a smart card, a flash drive, a removable disk, etc.) that enables the user(s) to customize the implementation of incubator system 10. Other exemplary input devices and techniques adapted for use with incubator system 10 as user interface 120 include, but are not limited to, an RS-232 port, RF link, an IR link, modem (telephone, cable, Ethernet, internet or other). In short, any technique for communicating information with incubator system 10 is contemplated as user interface 120.

Electronic storage 130 of incubator system 10 in FIG. 3 comprises electronic storage media that electronically stores information. The electronic storage media of electronic storage 130 may include one or both of system storage that is provided integrally (i.e., substantially non-removable) with incubator system 10 and/or removable storage that is removably connectable to incubator system 10 via, for example, a port (e.g., a USB port, a Fire Wire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables incubator system 10 to function properly. For example, electronic storage 130 may record or store one or more vital signs (as discussed elsewhere herein), air quality measurements, and/or other information. Electronic storage 130 may be a separate component within incubator system 10, or electronic storage 130 may be provided integrally with one or more other components of incubator system 10 (e.g., processor 110).

Processor 110 of incubator system 10 in FIG. 3 is configured to provide information processing capabilities in incubator system 10. As such, processor 110 includes one or more of a digital processor, an analog processor, a digital circuit designed to process information, an analog circuit designed to process information, a state machine, and/or other mechanisms for electronically processing information. Although processor 110 is shown in FIG. 3 as a single entity, this is for illustrative purposes only. In some implementations, processor 110 includes a plurality of processing units.

As is shown in FIG. 3, processor 110 is configured to execute one or more computer program modules. The one or more computer program modules include one or more of a parameter determination module 111, a light module 112, a notification module 113, and/or other modules. Processor 110 may be configured to execute modules 111, 112, and/or 113 by software; hardware; firmware; some combination of software, hardware, and/or firmware; and/or other mechanisms for configuring processing capabilities on processor 110.

It should be appreciated that although modules 111, 112, and 113 are illustrated in FIG. 3 as being co-located within a single processing unit, in implementations in which processor 110 includes multiple processing units, one or more of modules 111, 112, and/or 113 may be located remotely from the other modules. The description of the functionality provided by the different modules 111, 112, and/or 113 described below is for illustrative purposes, and is not intended to be limiting, as any of modules 111, 112, and/or 113 may provide more or less functionality than is described. For example, one or more of modules 111, 112, and/or 113 may be eliminated, and some or all of its functionality may be provided by other ones of modules 111, 112, and/or 113. Note that processor 110 may be configured to execute one or more additional modules that may perform some or all of the functionality attributed below to one of modules 111, 112, and/or 113.

Parameter module 111 of incubator system 10 in FIG. 3 may be configured to determine one or more status parameters, medical parameters, and/or other parameters from output signals generated by sensor(s) 142. One or more status parameters may be related to the presence and/or position of infant 106 within cavity 11. One or more status parameters may be related to air quality within cavity 11. One or more medical parameters may be related to monitored vital signs of infant 106, and/or other medical parameters of infant 106. Other parameters may be related to the environment inside or outside cavity 11, such as, e.g., air temperature, or the presence of UV radiation. Some or all of this functionality may be incorporated or integrated into other computer program modules of processor 110.

Light module 112 of incubator system 10 in FIG. 2 may be configured to control one or more UV light sources 20. Control by light module 112 may include one or more of an on-off switch, control of the controllable level of intensity, the controllable direction and/or angle of illumination, the controllable selection of illumination spectra, and/or other controllable illumination characteristics and/or illumination parameters of one or more UV light sources 20. In embodiments that include a secondary UV light source 40 (see e.g. system 10a in FIG. 4), light module 112 may be configured to control operation of secondary UV light source 40 based, at least, on a determination that infant 106 is not present within cavity 11. Such a determination may be based on information conveyed through output signals generated by one or more sensors 142.

By way of illustration, FIG. 4 schematically illustrates an incubator system 10a that includes a secondary UV light source 40. Incubator system 10a includes a secondary path 45 from ambient air into cavity 11 that is blockable. In some embodiments, secondary path 45 may be formed by base 2, e.g. in conjunction with walls 4. For example, secondary path 45 may be opened when walls 4 (jointly) are manually lifted (e.g., by a nurse) to place infant 106 in cavity 11. Secondary path 45 may be blocked and/or closed, when walls 4 rest on and/or engage with base 2. In some embodiments, secondary path 45 may be formed along the top edges of walls 4, e.g. by a lid that can be opened and closed. One or more sensors 142 of incubator system 10a may generate one or more output signals conveying blockage information related to whether secondary path 45 is currently blocked. Operation of light module 112 may be based on the blockage information, for example to control operation of secondary UV light source 40.

Notification module 113 of incubator system 10 in FIG. 3 may be configured to determine whether infant 106 is present within cavity 11 as based on the presence information conveyed by one or more output signals that are generated by one or more sensors 142. Notification module 113 may be configured to determine whether secondary path 45 is blocked, e.g. based on blockage information conveyed by one or more output signals that are generated by one or more sensors 142. Determinations by notification module 113 may include a determination that the incubator system 10a is closed, a feature within the incubator walls is activated to absorb or reflect UV radiation (e.g. liquid crystals may be activated to block transmission of UV radiation through the incubator walls), and/or the exterior of incubator system 10a is covered (e.g. with a protective tarp and/or cover), and/or other determinations that indicate UV radiation 41 will not impinge on anyone or anything unintentionally. Determinations by notification module 113 may be used by other components of incubator system 10 or incubator system 10a, e.g. by light module 112 to control secondary UV light source 40. Notification module 113 may be configured to present a notification to a user based on purification information conveyed by one or more output signals that are generated by one or more sensors 142. Purification information may be related to air quality within cavity 11.

Figure 5:
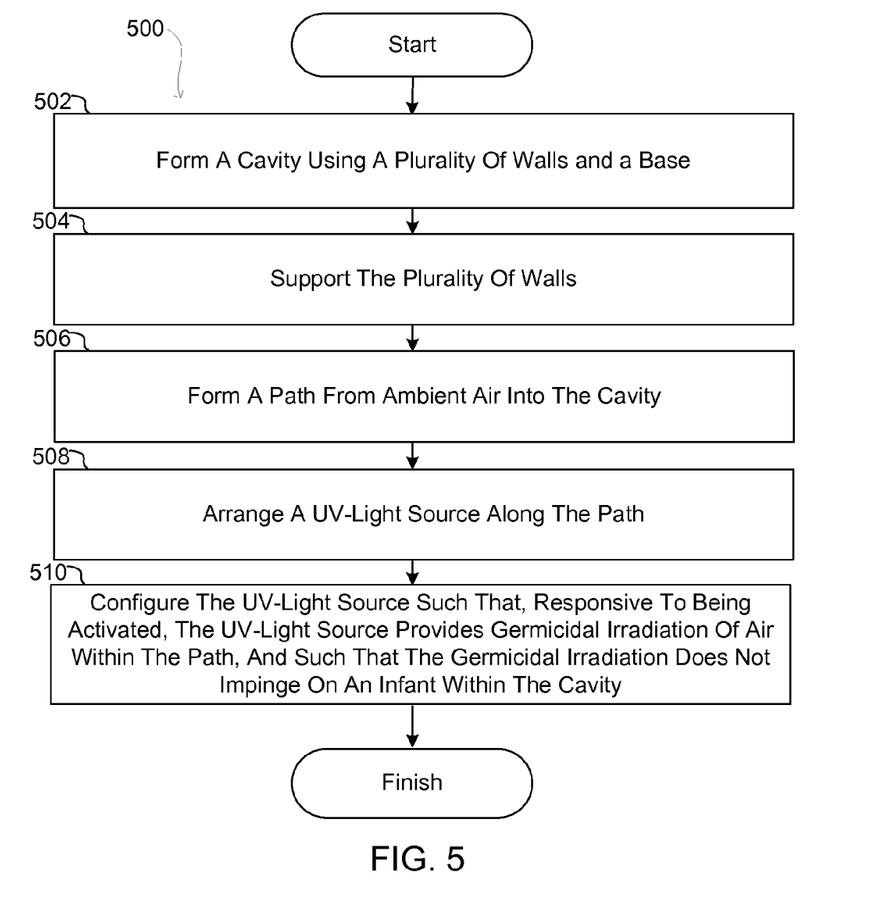
FIG. 5 illustrates a method for providing purification within an incubator system.

FIG. 5 illustrates a method for providing purification within an incubator system. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting. In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, a cavity is formed. In one embodiment, operation 502 is performed using a plurality of walls and a base similar to or substantially the same as plurality of walls 4 and base 2 (shown in FIG. 2 and described above).

At an operation 504, the plurality of walls is supported. In one embodiment, operation 504 is performed by a base similar to or substantially the same as base 2 (shown in FIG. 2 and described above).

At an operation 506, a path is formed from ambient air into the cavity. In one embodiment, operation 506 is performed by a path similar to or substantially the same as path 22 (shown in FIG. 2 and described above).

At an operation 508, a UV light source is arranged along the path. In one embodiment, operation 508 is performed by a UV light source similar to or substantially the same as UV light source 20 (shown in FIG. 2 and described above).

At an operation 510, the UV light source is configured such that, responsive to the first UV light source being activated, the first UV light source provides germicidal irradiation of air within the path, and such that the germicidal irradiation does not impinge on an infant within the cavity. In one embodiment, operation 510 is performed by a UV light source similar to or substantially the same as UV light source 20 (shown in FIG. 2 and described above).

Figure 6:
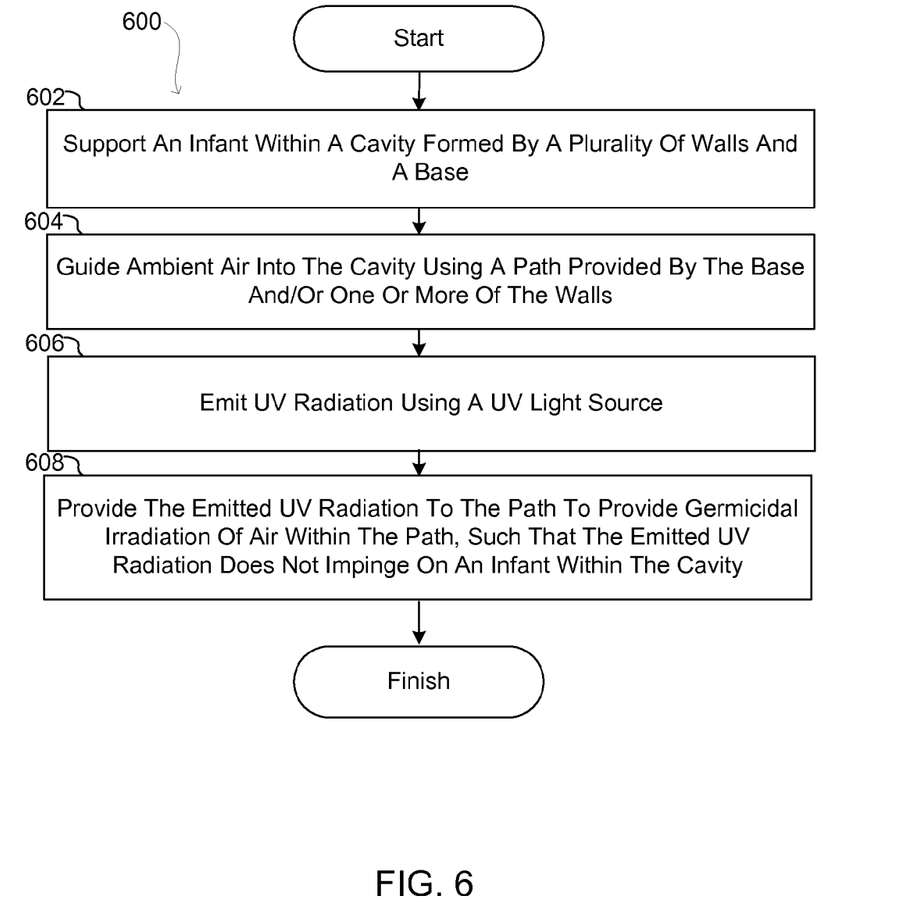
FIG. 6 illustrates a method for providing purification within an incubator system.

FIG. 6 illustrates a method for providing purification within an incubator system. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting. In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, an infant is supported within a cavity formed by a plurality of walls and a base. In one embodiment, operation 602 is performed using a plurality of walls and a base similar to or substantially the same as plurality of walls 4 and base 2 (shown in FIG. 2 and described above).

At an operation 604, ambient air is guided into the cavity using a path provided by the base and/or one or more of the walls. In one embodiment, operation 604 is performed by a path similar to or substantially the same as first path 22 (shown in FIG. 2 and described above).

At an operation 606, UV radiation is emitted using a UV light source. In one embodiment, operation 606 is performed by a UV light source similar to or substantially the same as UV light source 20 (shown in FIG. 2 and described above).

At an operation 608, the emitted UV radiation is provided to the path to provide germicidal irradiation of air within the path, such that the emitted UV radiation does not impinge on an infant within the cavity. In one embodiment, operation 608 is performed by a UV light source similar to or substantially the same as UV light source 20 (shown in FIG. 2 and described above).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An infant incubator system configured to purify air, comprising:
    a plurality of walls and a base, the base supporting the walls, the base and walls forming a cavity, wherein the base and/or one or more of the walls provide a first path from ambient air into the cavity;
    at least one sensor configured to determine presence of the infant within the cavity;
    a first ultra-violet light source arranged along the first path and configured such that, responsive to the first UV light source being activated, the first UV light source provides germicidal irradiation of air within the first path, and such that UV radiation emitted from the first UV light source substantially does not impinge on the infant within the cavity; and
- a second UV light source arranged and configured such that, responsive to the second UV light source being activated, the second UV light source emits UV radiation to provide germicidal irradiation within the cavity, wherein the second UV light source is activated responsive to a determination by the at least one sensor that the infant is not present within the cavity.

2. The incubator system of claim 1, further comprising one or more processors configured to execute computer program modules, the computer program modules comprising a light module configured to control operation of the first UV light source and the second UV light source.

3. The incubator system of claim 1, further comprising: an air circulator device configured to circulate air within the cavity, wherein the first UV light source is further arranged to provide germicidal irradiation for air circulated within the cavity.

4. The incubator system of claim 2, further comprising:
- one or more sensors that generate one or more output signals conveying presence information related to whether an infant is present within the cavity; and
- a notification module configured to determine whether an infant is present within the cavity as based on the presence information;
- wherein the light module is further configured to control operation of the second UV light source based on one or more determinations by the notification module.

5. An incubator system configured to purify air, comprising:
- a plurality of walls and a base, the base supporting the walls, the base and walls forming a cavity, wherein the base and/or one or more of the walls provide a first path from ambient air into the cavity;
- a first ultra-violet light source arranged along the first path and configured such that, responsive to the first UV light source being activated, the first UV light source provides germicidal irradiation of air within the first path, and such that UV radiation emitted from the first UV light source substantially does not impinge on an infant within the cavity;
- a second UV light source arranged and configured such that, responsive to the second UV light source being activated, the second UV light source emits UV radiation to provide germicidal irradiation within the cavity;
- one or more processors configured to execute computer program modules, the computer program modules comprising a light module configured to control operation of the first UV light source and the second UV light source;
- one or more sensors that generate one or more output signals conveying presence information related to whether an infant is present within the cavity;
- a notification module configured to determine whether an infant is present within the cavity as based on the presence information;
- wherein the light module is further configured to control operation of the second UV light source based on one or more determinations by the notification module;
- a second path from ambient air into the cavity that is blockable; and
- one or more sensors that generate one or more output signals conveying blockage information related to whether the second path is blocked,
- wherein the notification module is further configured to determine whether the second path is blocked as based on the blockage information.

6. The incubator system of claim 2, further comprising one or more sensors that generate one or more output signals conveying purification information related to air quality within the cavity, wherein the light module is configured to control operation of the first UV light source based on the purification information.

* * * * *